US005700475A

United States Patent [19]
Massman et al.

[11] Patent Number: 5,700,475
[45] Date of Patent: Dec. 23, 1997

[54] STABILIZED PESTICIDAL COMPOSITIONS AND THEIR USE

[75] Inventors: Brent D. Massman, St. Louis; Maria L. Miller, Manchester, both of Mo.

[73] Assignee: Monsanto Company, St. Louis, Mo.

[21] Appl. No.: 580,867

[22] Filed: Dec. 29, 1995

[51] Int. Cl.$^6$ ........................................... A01N 25/28
[52] U.S. Cl. ...................... 424/408; 424/418; 424/419; 424/420; 504/127; 514/75
[58] Field of Search ...................... 424/405, 408, 424/409–417; 504/127, 130, 148; 514/75, 241, 272, 630, 963

[56] References Cited

U.S. PATENT DOCUMENTS

| | | | |
|---|---|---|---|
| 3,091,567 | 5/1963 | Wurzburg et al. | 167/42 |
| 3,455,838 | 7/1969 | Marotta | 252/316 |
| 4,534,783 | 8/1985 | Beestman | 71/27 |
| 4,722,838 | 2/1988 | Tocker | 424/81 |
| 5,073,191 | 12/1991 | Misselbrook et al. | 71/121 |
| 5,229,122 | 7/1993 | Chadwick et al. | 424/408 |
| 5,317,004 | 5/1994 | Misselbrook et al. | 504/116 |

FOREIGN PATENT DOCUMENTS

| | | |
|---|---|---|
| 0 548 901 A1 | 12/1992 | European Pat. Off. . |
| 2 025 887 | 7/1979 | United Kingdom . |

OTHER PUBLICATIONS

"Microencapsulation", *Encyclopedia of Polymer Science and Engineering*, vol. 9, 2nd Ed. pp. 724, 731–733 (1987).
Anderson et al., "Microencapsulation", *Management Reports*, pp. 1, 46, 47, 1963.
*Encyclopedia of Polymer Science and Technology*, vol. 8, p. 719 (1968).
Kondo, A., "Microcapsule Processing and Technology", *Applications and Studies of Microcapsules*, Marcel Dekker, Inc., pp. 18–19, 157 (1979).

*Primary Examiner*—Neil S. Levy
*Attorney, Agent, or Firm*—Jon H. Beusen; Mary Jo Boldingh; Harold N. Wells

[57] ABSTRACT

Flowable composites are disclosed which comprise a) microcapsules comprising one or more non-aqueous pesticidally active compositions enclosed in an inert water-soluble wall material; b) a non-aqueous liquid in an amount sufficient to maintain the composite flowable; the non-aqueous pesticidally active composition and the non-aqueous liquid being reactive with each other and the inert water-soluble wall material being insoluble in and impermeable to the non-aqueous liquid and the pesticidally active composition. Also disclosed are composites in which the pesticidally active compositions are internally-reactive in the presence of a non-aqueous liquid or solvent. Processes for production of the composites and their utilization as pesticides are also disclosed.

9 Claims, No Drawings

STABILIZED PESTICIDAL COMPOSITIONS AND THEIR USE

FIELD OF THE INVENTION

The invention relates to stabilized compositions or formulations useful for pesticidal purposes, to a process for the production of such compositions, and to processes for use of the compositions in controlling pests.

BACKGROUND OF THE INVENTION

The use of membranes, coatings, and capsules for enclosure of components is known in the preparation of formulations for use in pesticidal applications. For example, U.S. Pat. No. 4,534,783 (Beestman, et al) discloses a variety of prior art encapsulated compositions and encapsulation procedures. European patent application 0 548,901 A1 (1992) describes agricultural compositions utilizing microcapsules comprising water-soluble coating materials, and discloses a procedure for making such microcapsules. The application emphasizes the production of particles less than 50 microns, because a microcapsule "having a diameter of not less than 50 microns has bad adhesion to plants as a dust formulation and fails to show the effect of the active ingredients." In addition, according to the application, if the larger particles are mixed with other active ingredients, "a remarkable difference in density results in difficulty in sufficient mixing."

U.S. Pat. No. 5,229,122 (Chadwick et al) discloses formulations "comprising microcapsules containing a pesticide the same or another pesticide in a non-encapsulated form", stating that an upper limit of fifty percent of the pesticide in the non-encapsulated form is preferred. According to this patent, two mutually incompatible pesticides may be included in the formulation: "a less-stable (sic) non-encapsulated one, with a more stable encapsulated one, so that the non-encapsulated one will have degraded or dispersed by the time that at least the bulk of the encapsulated pesticide emerges." Additionally, the patent discloses that formulations "may take the form of dry granular matter or aqueous suspensions" or, alternatively, "a water-soluble wall material may be used in a non-aqueous solvent."

Notwithstanding the well developed state of the art with respect to formulation of pesticidal compositions, there has remained a need for flowable composite formulations of mutually reactive pesticidally active species, combinations of reactive pesticidally active species with reactive non-aqueous liquids, and for combinations of non-aqueous liquids and pesticidally active compositions which are internally reactive in the presence of the non-aqueous liquids. More particularly, there has existed a need for a flowable formulation containing a reactive non-aqueous pesticidally active material in which the reactive components of the formulation are stabilized to the extent that any reactive pesticidal component does not degrade or lose effectiveness during storage because of its reactivity or the reactivity of another component of the formulation. The invention addresses these needs.

SUMMARY OF THE INVENTION

Accordingly, the invention, in one embodiment, relates to a flowable composite comprising a) microcapsules comprising a non-aqueous pesticidally active composition enclosed in an inert water-soluble wall material; b) a non-aqueous liquid in an amount sufficient to maintain the composite flowable; the non-aqueous pesticidally active composition and the non-aqueous liquid being reactive with each other and the inert water-soluble wall material being insoluble in the non-aqueous liquid and the pesticidally active composition. More particularly, the invention relates to a flowable composite comprising a) microcapsules comprising a non-aqueous pesticidally active composition enclosed in an inert water-soluble wall material; b) a non-aqueous liquid which is reactive with the non-aqueous pesticidally active composition; the inert water-soluble wall material being insoluble in the non-aqueous pesticidally active composition and in the non-aqueous liquid, and the non-aqueous liquid being present in an amount sufficient to maintain the composite flowable.

This embodiment of the invention, therefore, comprises a novel stable, flowable pesticidal formulation containing non-aqueous compositions which otherwise would react with each other. The term "reactive", with respect to the pesticidally active and non-aqueous liquid components of the composites of the invention, is understood to encompass the relatively "slow" reaction of one or more of the components utilized, which would degrade the formulation over a significant period of time, as well as the spontaneous or substantially prompt reaction of one or more components in the pesticidal composition and one or more components of the non-aqueous liquid. Additionally, "reactive" pesticidally active compositions of the invention are understood to include those pesticidally active compositions whose molecules are internally reactive or which undergo internal reaction, i.e., intramolecular rearrangement, in the presence of "reactive" non-aqueous liquids. The latter "reactive" non-aqueous liquids, while not necessarily "reactive" in a classic chemical sense, are so considered herein, in that they cause or promote this rearrangement by physical or chemical interaction, e. g., by dissolution, and, in the absence of the invention, directly or indirectly cause partial or complete loss of efficacy of the pesticidally active composition. Finally, reference herein to a component being "reactive with" another does not imply that the latter component is not reactive with the first mentioned component, those skilled in the art recognizing that both components participate in the "reaction".

In most instances, the ratio of the non-aqueous liquid to all solids in the composite will be greater than 1:1 by weight, and preferably will be at least 1.1:1 by weight, most preferably, 1.1:1 to 9.0:1 by weight. Unless otherwise specified, all ratios or percentages specified herein are by weight. As employed herein, the phrase "pesticidally active composition" is understood to include the presence of more than one pesticidally active material or compound, and refers to a composition used or useful in controlling pests, including, but not limited to, one or more herbicides, miticides, fungicides, nematocides, rodenticides, algicides, miticides, mildewicides, slimicides, attractants, and the like. The phrase is further to be understood as permitting or including, optionally, the presence of non-aqueous solvents, adjuvants, surfactants, diluents, carriers, preservatives, extenders, etc. The encapsulated pesticidally active composition may be solid or liquid. The term "non-aqueous", with respect to both the pesticidally active composition and the reactive non-aqueous liquid, does not necessarily require absolute absence of moisture, provided that there is insufficient free moisture in either to dissolve or degrade the water-soluble wall material to any significant extent, it being understood that some chemically bound water may be present in the respective composition or liquid and that the degree of stability achieved by the invention will be affectedly the amount of free moisture present. As will be understood by those skilled in the art, addition of water or aqueous liquid will release the encapsulated pesticidally active composition, allowing the pesticidal action thereof.

In preferred aspects of the invention, the reactive pesticidally active composition and the reactive non-aqueous liquid are herbicides which would otherwise react and lose their efficiency.

In a further embodiment, the invention relates to a process for providing flowable stabilized pesticidal composites containing a non-aqueous pesticidally active composition and a reactive non-aqueous liquid comprising a) encapsulating a pesticidally active composition in an inert water-soluble wall material, forming a plurality of discrete microcapsules containing said pesticidally active composition; b) blending microcapsules from step a) with a non-aqueous liquid which is reactive with the pesticidally active composition and in which the inert water-soluble wall composition is insoluble, the amount of the reactive non-aqueous liquid being sufficient to produce with the microcapsules a flowable composition. Other components may be added to the flowable composition if desired.

In yet further embodiments, the invention relates to processes for the control of pests utilizing the novel pesticidal formulations or composites of the invention. The pesticidal formulations or composites may be applied directly to the pest or to a locus to be protected, or may be blended first with a carrier liquid.

DETAILED DESCRIPTION OF THE INVENTION

As described more fully hereinafter, the reactive non-aqueous pesticidally active compositions employed in the invention may be selected from a wide variety of compounds or mixtures thereof. In addition to the solvents, diluents, etc., which also may be encapsulated with the pesticidally active composition, the pesticidally active composition my further comprise additional liquid or solid materials not technically described as pesticidal, such as plant growth regulators, soil nutrients, safeners, antidotes, and the like, to the effect that a useful flowable composite for agricultural or household use may be presented.

As used herein, the term "flowable", in delimiting the composite of the invention, is understood to cover a range of mass characteristics or properties. These properties will extend, for example, in the case of a large proportion of non-aqueous liquid, from a thin liquid, to a viscous or elastic liquid, such as an elastic gel, in the case of a higher proportion of microcapsules, or the presence of fillers or gelling and paste-forming agents. In all cases, however, sufficient non-aqueous liquid will be present to form a coherent mass in which there is freedom of movement among the particles and change of form under the application of force.

An important aspect of the invention is the encapsulation of the pesticidally active composition in discrete particles or microcapsules. As used herein, the terms "microcapsule" or "microcapsules" refers to capsules or enclosed particles having a mean diameter of less than 4 mm, preferably less than 2 mm. Commonly, however, the particles will have a mean diameter of between 1 and 100 microns, most preferably between 5 and 50 microns.

As indicated, a microcapsule may comprise or enclose more than one pesticidally active compound or material, provided the pesticidally active compounds do not react with each other to any significant extent. Further, the flowable composites of the invention may comprise a plurality of types of microcapsules, each of which may utilize the same or different water-soluble wall material, and each of which may have the same or a different pesticidally active composition.

The particular procedure for encapsulating the pesticidally active composition in the inert water-soluble wall material is a matter within the ambit of those skilled in the art, and depends largely on the particular pesticidally active composition and the inert water-soluble encapsulating material chosen. In general, any encapsulation procedure which produces an inert water-soluble coating which is insoluble in the pesticidally active composition and the reactive non-aqueous liquid, is impermeable to the entrapped reactive pesticidally active composition and the reactive non-aqueous liquid, does not significantly degrade or irreversibly inactivate the pesticidally active composition, and produces particles that can be suspended in the reactive non-aqueous liquid, may be used. *The Encyclopedia of Polymer Science and Engineering*, Volume 9, Second Edition, 1987, p.p. 724–745, John Wiley & Sons, Inc. describes a number of suitable prior methods of encapsulation which my be adapted to the invention. Preferably, the reactive pesticidally active composition will first be dissolved, emulsified, or dispersed into a solution of the water-soluble encapsulating material, and the resulting solution, emulsion, or dispersion will be dried, such as by spray drying or other suitable technique. As indicated, other techniques, such as coacervation or air suspension coating, may be used.

In general, any encapsulation material which produces an inert water-soluble coating or wall structure insoluble in and impermeable to the entrapped reactive pesticidally active composition and the reactive non-aqueous liquid, and which is capable of producing coated particles or capsules that can be suspended in the reactive non-aqueous liquid, may be used. Designation of the wall material or structure as "inert" is understood as requiring that the wall structure or coating does not significantly react with the non-aqueous liquid or the pesticidally active composition, or degrade or irreversibly inactivate the pesticidally active composition or reactive non-aqueous liquid. As a practical matter, selection of the inert wall or encapsulation material is made in view of the properties, particularly the solvent properties, of the reactive pesticidally active composition and the reactive non-aqueous liquid. As indicated, selection is made of inert water-soluble wall material or materials which are insoluble, i.e., which have little or no solubility, in the pesticidally active composition and the reactive non-aqueous liquid. The terms "insoluble" and "impermeable" are thus employed in their usual sense, in that absolute insolubility or impermeability is not required, so long as significant dissolution of the coating or wall structure, or significant passage of composite components therethrough, does not occur. The inert water-soluble wall structure or coating may be a composite; i.e., more than one suitable inert coating or encapsulating material may be employed, provided at least one coating or wall structure is impermeable to the pesticidally active composition and the non-aqueous liquid. Suitable water-soluble encapsulating materials, such as polyvinyl pyrrolidone, polyvinyl alcohol, hydroxyethyl cellulose, and other synthetic of natural water-soluble polymers, oligomers, gums, and mixtures thereof, may be used. Preferred encapsulating materials are water-soluble gum arabic, modified starches, maltodextrins, and mixtures thereof.

The reactive non-aqueous liquid is selected for the particular purpose desired, in light of the teachings and requirements set forth herein. For example, the reactive non-aqueous liquid may be a pesticidally active composition, as defined herein, or may be selected from organic liquids, solvents, adjuvants, surfactants, diluents, carriers, preservatives, extenders, etc., of appropriate characteristics. The invention thus makes possible the combination of a wide variety of components to form flowable multi-component composites where individual components thereof would otherwise react, as understood herein, with each other. In most instances, applicability of the invention to a given possible combination is determinable by combination of the components and assessment of the stability of the mixture. By way of example, the invention is valuable in combining in a flowable composition (as pesticidally active composition and non-aqueous liquid) components such as reactive sulfonyl ureas and acetanilides, esters, amides, alcohols, amines, or ethers, or reactive triazines and organophosphates. Suitable composite pairs include, but are not limited thereto, bensulfuron methyl and molinate; (2,4-dichlorophenoxy) acetic acid and thifensulferon methyl; (2,4-dichlorophenoxy) acetic acid and methyl 2-[[[[(N-4-methoxy-6-methyl)-1,3,5-triazin-2-yl)-N-methylamino]carbonyl]amino]sulfonyl]benzoate; halosulfuron and acetochlor; (2,4-dichlorophenoxy) acetic acid and metsulfuronmethyl; maneb and benomyl; manoseb and benomyl; glyphosate and metsulfuron methyl; tralomethrin and monocrotophos; tralomethrin and dimethoate; bromooxynil and N-[4,6-dimethoxypyrimidine-2-yl)amino]carbonyl]-3-(ethylsulfonyl)-2-pyrimidinesulfonamide; bromoxynil and methyl 2-[[[[N-4-methyl-6-methoxy-1,3,5-triazin-2-yl)-N-methylamino]carbonyl]amino]sulfonyl]benzoate; and bromoxynil and methyl 2-[[[[N-4-methoxy-6-methyl-1,3,5-triazin-2-yl)-N-methylamino]carbonyl]amino]sulfonyl] benzoate. Internally-reactive compositions to which the invention may be applied include certain sulfonyl ureas, such as halosulfuron, in such non-aqueous liquids as lactones, e.g., butyrolactone, or in n-methylpyrrolidone.

The concentration of pesticidally active composition present in the capsule or particle may range from 100 percent to quite small amounts, e.g., 0.5 percent, and similar concentrations of pesticidally active composition may be employed in or as the reactive non-aqueous liquid. In general, when the reactive non-aqueous liquid comprises a pesticidally active composition, the reactive non-aqueous liquid will comprise at least 55 percent of the total amount of the pesticide in the composite, preferably from 60 percent to 99 percent. The composite may comprise other non-reactive solids, provided the ratios of non-aqueous reactive liquid to total solids specified previously are maintained so that the composite product is flowable.

So formulated, the composites may be applied or used directly for pesticidal purposes, or they my be diluted with a non-aqueous or aqueous liquid. If diluted with an aqueous liquid, such as water or water containing surfact-ants, the encapsulated pesticidally active composition will be released. According to the invention, the composites will be applied, in any case, to the species sought to be eradicated, or to a locus to be protected, in a pesticidally effective amount. In each case, a pesticidally effective amount will be that amount needed to give the desired control, i.e., the eradication or elimination of the undesired species. For example, in the control of weeds or undesired vegetation, herbicidal composites of the invention will be applied in an herbicidally effective amount, an amount sufficient to eliminate the weeds or undesired species of vegetation. Similarly, insecticidal composites of the invention will be applied in an amount sufficient to control the undesired insect, i.e., an insecticidal amount.

The following examples illustrate the preparation and testing of composites which contain halosulfuron (methyl-3-chloro-5-(4,6-dimethoxy pyrimidin-2-ylcarbamoylsulfamoyl)-1-methylpyrazol-4-carboxylate) and acetochlor/furilazole emulsifiable concentrate. The advantage of the invention is evident, since a simple premix containing halosulfuron and acetochlor/furilazole emulsifiable concentrate decomposes rapidly when stored at moderate temperatures.

EXAMPLE I

One hundred grams of halosulfuron were mixed into one hundred fifty grams of 6.7 percent gum arabic solution. The mixture was then milled for one hour at 5000 rpm in an Eiger Minimill 50 which contained 40 milliliters of 1.0 to 1.6 mm silica-zirconia milling media, ice water being utilized in the cooling jacket to maintain an internal mill temperature of about 50° C. An additional twenty-five grams of 6.7 percent gum arabic solution were added and milling was then continued for an additional 30 minutes. A final addition of one hundred fifty grams of the 6.7 percent gum arabic solution was then made and the dispersion was removed from the mill.

Accompanied by stirring, 85.5 grams of gum arabic were then combined with ninety grams of the milled halosulfuron dispersion. Water was added in an amount of 124.5 grams to the mixture, and the mixture was mixed for one hour to insure full hydration of the gum arabic. The suspension formed was then spray dried in a Niro portable spray drier fitted with a rotary atomizer. The drying conditions were 29 grams/minute spray rate, 200° C. inlet temperature, and 110° C. outlet temperature. The product particles had a mean particle size of 52 microns, a moisture of 2.7 percent, and an assay of 20.1 percent.

An acetochlor and MON 13900 Emulsifiable Concentrate (EC) was prepared by combining 82.45 parts of acetochlor, 7.8 parts furilazole, 6.5 parts Stepan 1690-92A non-ionic surfactant and 3.25 parts Stepan 1690-92N anionic surfactant, available from Stephan Chemical Company.

A mixture of 11 parts microencapsulated halosulfuron and 89 parts of EC was prepared. The mixture was placed in temperature controlled ovens at 40C and 50C for 4 weeks. Stability results are shown in Table I, as a percentage recovery of the halosulfuron from the acetochlormixture. For comparison, 2.5 parts unencapsulated halosulfuron and 97.5 parts of EC were prepared. The mixture was placed in a temperature controlled oven at 40 C for 4 weeks. Stability results are shown in Table I, shown as the percentage recovery of the halosulfuron from the acetochlormixture, is shown in Table I.

EXAMPLE II

One hundred grams of halosulfuron were mixed into one hundred fifty grams of 6.7 percent gum arabic solution. The mixture was then milled for one hour at 5000 rpm in an Eiger Minimill 50 which contained 40 milliliters of 1.0 to 1.6mm silica-zirconia milling media, ice water being utilized in the cooling jacket to maintain a temperature of 50° C. An additional twenty-five grams of 6.7 percent gum arabic solution were added and milling was then continued for an additional 30 minutes. A final addition of one hundred fifty grams of the 6.7 percent gum arabic solution was then made and the dispersion was removed from the mill.

Accompanied by stirring, 120 grams of maltodextrin powder with a dextrose equivalent of 10 were then combined with 120 grams of the milled halosulfuron dispersion.

Water was added in an amount of 66 grams to the mixture, and the mixture was stirred for one hour. The suspension formed was then spray dried in a Niro portable spray drier fitted with a rotary atomizer. The drying conditions were 28 grams/minute spray rate, 200° C. inlet temperature, and 105° C. outlet temperature. The product particles had a mean particle size of 49 microns, a moisture of 2.8 percent, and an assay of 18.5 percent.

A mixture of 12 parts of the particles and 88 parts of acetochlor/furilazole emulsifiable concentrate was prepared. The mixture was divided into two portions, and the portions were placed into separate ovens and held at 40° C. and 50° C. for 4 weeks. Stability results are shown in Table I as a percentage recovery of the halosulfuron from the acetochlor mixture.

TABLE I

| | Sample | 40° C. | 50° C. |
|---|---|---|---|
| 1. | Halosulfuron, unencapsulated, plus Acetochlor/furilazole | 18% | — |
| 2. | Encapsulated halosulfuron, Example I | >99% | >99% |
| 3. | Encapsulated halosulfuron, Example II | >95% | >95% |

The results shown in Table I demonstrate enhanced stability for compositions prepared according to the invention.

When halosulfuron was encapsulated with various water-soluble encapsulating agents in a similar manner according to the invention, and blended with acetochlor/furilazole emulsifiable concentrate, stable flowable compositions were obtained. Stability results at 50° C. are recorded in Table II, shown as percent recovery (rounded to the nearest tenth) compared with control samples held at −25° C.

TABLE II

| Sample | 2 weeks | 4 weeks |
|---|---|---|
| Comparison at 40° C. (mixture of halosulfuron in acetochlor/furilazole) Encapsulated halosulfuron with Acetochlor/furilazole emulsifiable concentrate. | 45.1% | 17.8% |
| Gum Arabic | | |
| 10% halosulfuron | 99.5% | 100% |
| 20% halosulfuron | 97.3% | 98.2% |
| 30% halosulfuron | 96% | 93.6% |
| Capsul (™) (modified food starch) | | |
| 10% halosulfuron | 98.5% | 100.5% |
| 20% halosulfuron | 97.2% | 99.0% |
| Maltodextrin (10 Dextrose Equivalent):Gum Arabic | | |
| 1:2; 10% halosulfuron | 98.1% | 97.1% |
| 1:2; 20% halosulfuron | 100.0% | 99.0% |
| 1:1; 10% halosulfuron | 94.2% | 96.9% |
| 1:1; 20% halosulfuron | 98.6% | 99.1% |
| 2:1; 10% halosulfuron | | 95.9% |
| 2:1; 20% halosulfuron | | 89.6% |
| 4:1; 10% halosulfuron | | 96.3% |
| 4:1; 20% halosulfuron | | 96.1% |
| 19:1; 20% halosulfuron | 96.2% | 95.6% |
| Maltodextrin (5 Dextrose Equivalent):Gum Arabic | | |
| 1:2; 10% halosulfuron | 98.0% | 96.6% |
| 1:2; 20% halosulfuron | 85.2% | 86.5% |
| 1:1; 10% halosulfuron | 100.5% | 101.1% |
| 1:1; 20% halosulfuron | 96.7% | 97.6% |
| Maltodextrin (10 Dextrose Equivalent):Capsul | | |
| 15:1; 10% halosulfuron | 97.5% | 99% |
| 15:1; 20% halosulfuron | 98.9% | 98.3% |
| Maltodextrin (5 Dextrose Equivalent):Capsul | | |
| 1:1; 10% halosulfuron | | 99.0% |
| 1:1; 20% halosulfuron | | 97.2% |
| 2:1; 10% halosulfuron | | 99% |
| 2:1; 20% halosulfuron | | 97.6% |
| 4:1; 10% halosulfuron | | 95.9% |
| 4:1; 20% halosulfuron | | 99.5% |
| 15:1; 10% halosulfuron | 97.9% | 98.9% |
| 15:1; 20% halosulfuron | 96.1% | 99.5% |

The results shown in Table II demonstrate enhanced stability for compositions prepared according to the invention.

What is claimed:

1. A flowable composite comprising a) microcapsules having a mean diameter of less than 4 mm comprising a non-aqueous herbicidally active composition enclosed in an inert water-soluble wall material; and b) a non-aqueous herbicidal liquid in an amount sufficient to maintain the composite flowable; the non-aqueous herbicidally active composition and the non-aqueous herbicidal liquid being reactive with each other and the inert water-soluble wall material being insoluble in and impermeable to the herbicidally active composition and the non-aqueous herbicidal liquid.

2. The composition of claim 1 wherein the ratio of the non-aqueous liquid to solids in the composite is greater than 1:1.

3. The composition of claim 1 in which and the non-aqueous herbicidal liquid is present in an amount of at least 55 percent by weight.

4. The composition of claim 2 wherein the herbicidally active composition comprises a sulfonyl urea.

5. The composition of claim 4 wherein the reactive non-aqueous herbicidal liquid comprises an acetanilide.

6. The composition of claim 2 wherein the herbicidally active composition comprises halosulfuron and the non-aqueous herbicidal liquid comprises a mixture of acetochlor and furilazole.

7. A process for killing undesired vegetation comprising applying to the undesired vegetation or a locus to be protected an herbicidally effective amount of a flowable composite comprising a) microcapsules having a mean diameter of less than 4 mm comprising a non-aqueous herbicidally active composition enclosed in an inert water-soluble wall material; and b) a non-aqueous herbicidal liquid in an amount sufficient to maintain the composite flowable; the non-aqueous herbicidally active composition and the non-aqueous herbicidal liquid being reactive with each other and the inert water-soluble wall material being insoluble in and impermeable to the herbicidally active composition and the non-aqueous herbicidal liquid.

8. A process for killing undesired vegetation comprising blending with an aqueous liquid, in an amount sufficient to form a herbicidal admixture, a flowable composite comprising a) microcapsules having a mean diameter of less than 4 mm comprising a non-aqueous herbicidally active composition enclosed in an inert water-soluble wall material; and b) a non-aqueous herbicidal liquid in an amount sufficient to maintain the composite flowable; the non-aqueous herbicidally active composition and the non-aqueous herbicidal liquid being reactive with each other and the inert water-soluble wall material being insoluble in and impermeable to the herbicidally active composition and the non-aqueous herbicidal liquid, and applying to the undesired vegetation or a locus to be protected an herbicidally effective amount of said admixture.

9. The composition of claim 8 wherein the herbicidally active composition comprises halosulfuron and the non-aqueous herbicidal liquid comprises a mixture of acetochlor and furilazole.

* * * * *

UNITED STATES PATENT AND TRADEMARK OFFICE
CERTIFICATE OF CORRECTION

PATENT NO. : 5,700,475
DATED : December 23, 1997
INVENTOR(S) : Massman et al.

It is certified that error appears in the above-identified patent and that said Letters Patent is hereby corrected as shown below:

Column 8, Claim 3, line 48, delete "and".

Signed and Sealed this

Eighth Day of December, 1998

Attest:

BRUCE LEHMAN

*Attesting Officer*              *Commissioner of Patents and Trademarks*